(12) United States Patent
Joo et al.

(10) Patent No.: US 7,919,548 B2
(45) Date of Patent: Apr. 5, 2011

(54) STERICALLY HINDERED PHENOLIC PHOSPHONATES AND POLYCARBONATE RESIN COMPOSITION USING THE SAME

(75) Inventors: Beom Jun Joo, Seoul (KR); Min Soo Lee, Ansan-si (KR); Byun Kun Lee, Gunpo-si (KR)

(73) Assignee: Cheil Industries Inc., Gumi-si (KR)

( * ) Notice: Subject to any disclaimer, the term of this patent is extended or adjusted under 35 U.S.C. 154(b) by 30 days.

(21) Appl. No.: 12/273,762

(22) Filed: Nov. 19, 2008

(65) Prior Publication Data

US 2009/0149587 A1 Jun. 11, 2009

(30) Foreign Application Priority Data

Dec. 10, 2007 (KR) .................. 10-2007-0127462

(51) Int. Cl.
*C08K 5/5357* (2006.01)
*C07F 9/40* (2006.01)

(52) U.S. Cl. ........ 524/132; 524/130; 558/179; 558/214; 558/215

(58) Field of Classification Search .................. 524/130, 524/132; 558/179, 214, 215
See application file for complete search history.

(56) References Cited

U.S. PATENT DOCUMENTS

| | | | |
|---|---|---|---|
| 4,248,976 | A | 2/1981 | Clubley et al. |
| 4,692,488 | A | 9/1987 | Kress et al. |
| 5,061,745 | A | 10/1991 | Wittmann et al. |
| 7,569,629 | B2 | 8/2009 | Hong et al. |

FOREIGN PATENT DOCUMENTS

| | | | |
|---|---|---|---|
| JP | 57-105435 | * | 6/1982 |
| JP | 05-001084 | | 1/1993 |
| KR | 10-0560151 B1 | | 3/2006 |

OTHER PUBLICATIONS

Korean Office Action in counterpart Korean Application No. 10-2007-0127462, dated Mar. 31, 2009.

* cited by examiner

*Primary Examiner* — Peter Szekely
(74) *Attorney, Agent, or Firm* — Summa, Additon & Ashe, P.A.

(57) ABSTRACT

Disclosed herein is a sterically hindered phenolic phosphonate resin compound represented by the following Chemical Formula 1. The present invention also provides a polycarbonate resin composition including the sterically hindered phenolic phosphonate resin compound as a flame retardant.

[Chemical Formula 1]

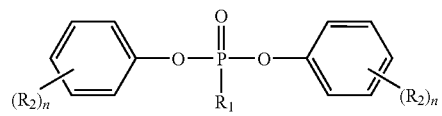

wherein $R_1$ is a $C_1$-$C_6$ alkyl group or a $C_6$-$C_{14}$ aryl group; each $R_2$ is independently a $C_1$-$C_6$ linear alkyl group or a $C_3$-$C_6$ branched alkyl group; and each n is independently 1-3.

24 Claims, 9 Drawing Sheets

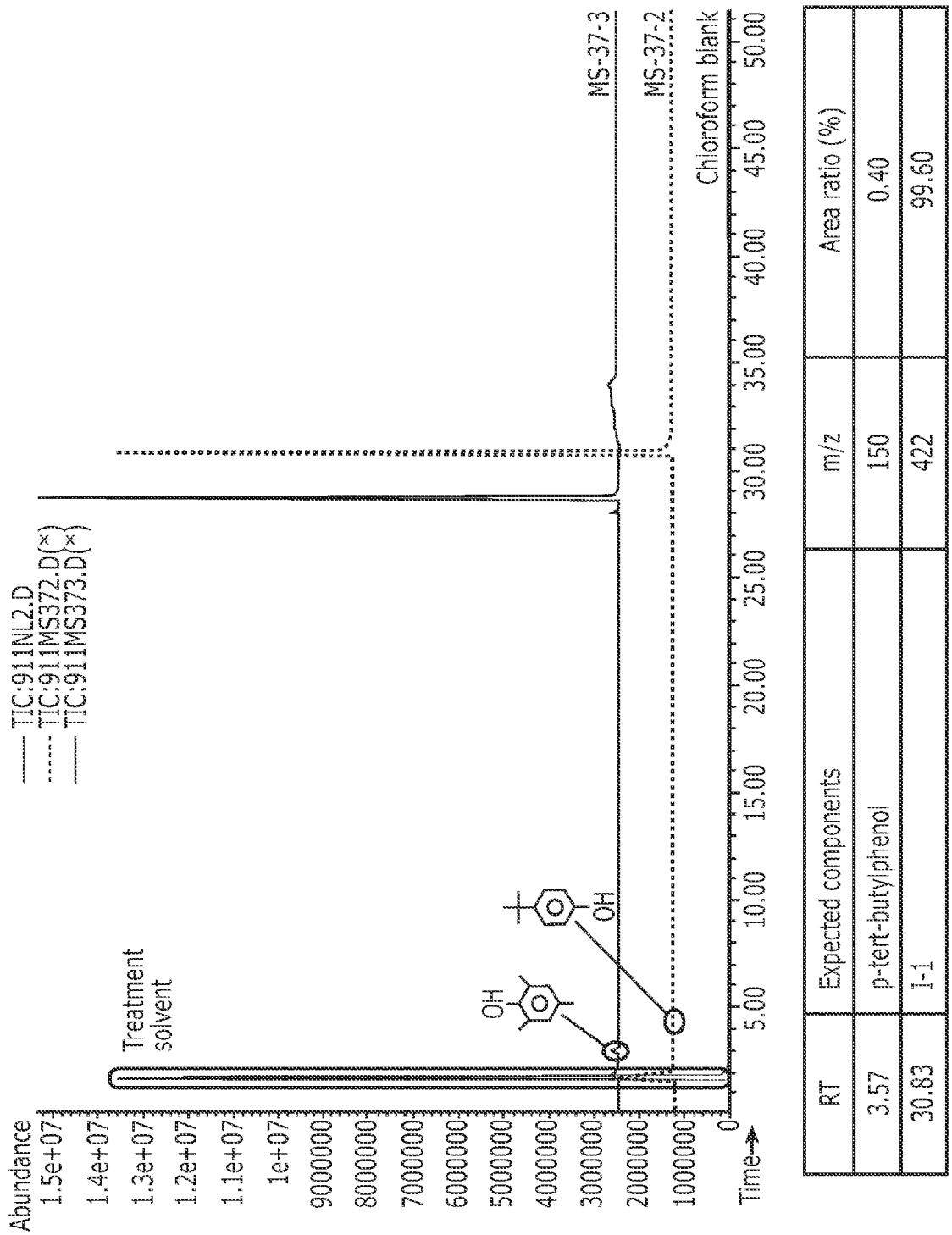

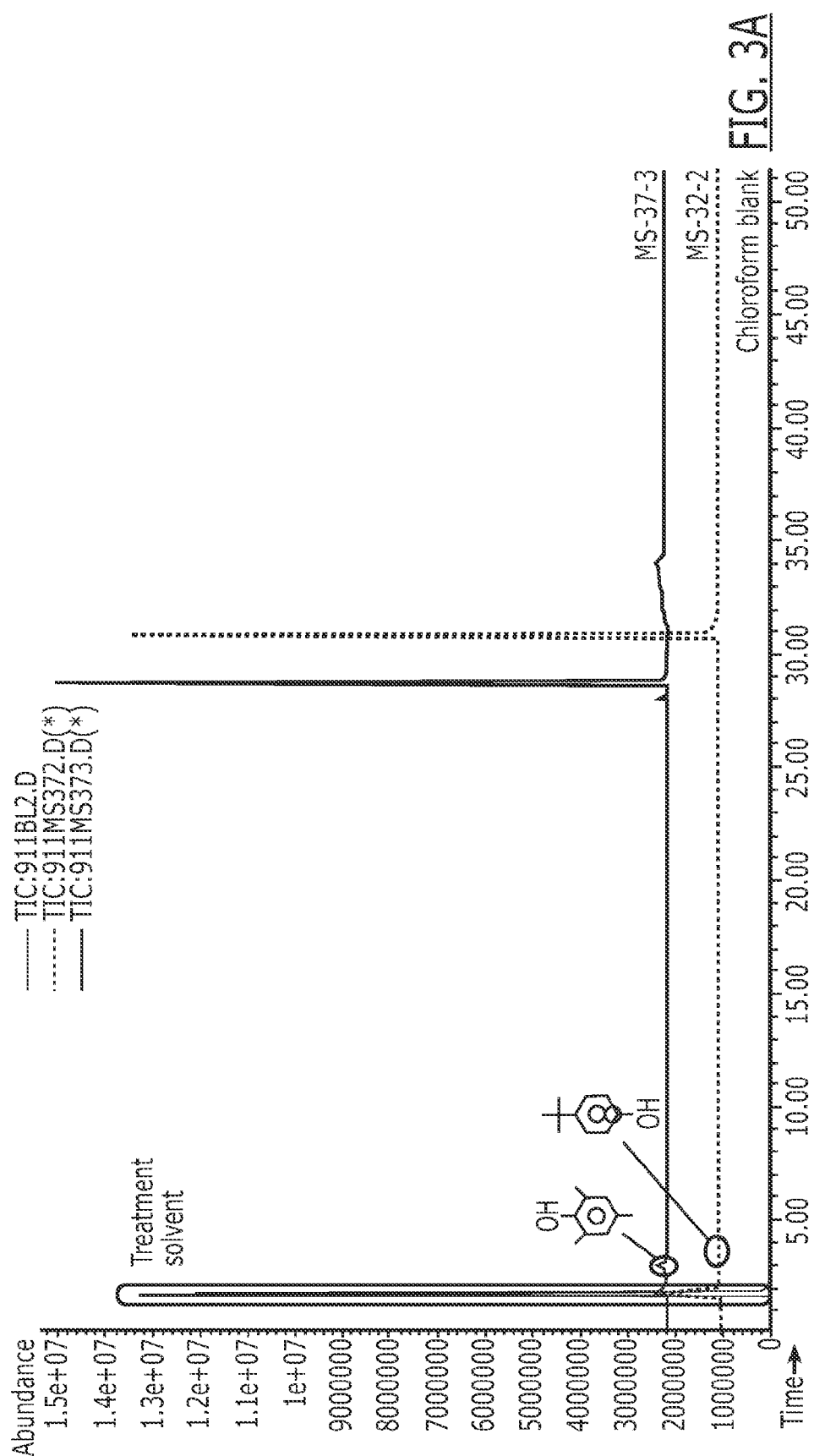

STERICALLY HINDERED PHENOLIC PHOSPHONATES AND POLYCARBONATE RESIN COMPOSITION USING THE SAME

CROSS-REFERENCE TO RELATED APPLICATION

This application claims priority from Korean Patent Application No. 10-2007-127462 filed on Dec. 10, 2007, in the Korean Intellectual Property Office, the disclosure of which is incorporated herein by reference in its entirety.

FIELD OF THE INVENTION

The present invention relates to a novel phosphorus-containing flame retardant and a non-halogen flameproof polycarbonate resin composition using the same. More particularly, the present invention relates to a sterically hindered phenolic phosphonate compound, a method of preparing the same, and a polycarbonate resin composition using the same as a flame retardant.

BACKGROUND OF THE INVENTION

Generally, polycarbonate and vinyl copolymer resin blend compositions can provide improved processability while maintaining high notched impact strength. Such resin blend compositions should also have good flame retardancy as well as high mechanical strength when used in the production of heat-emitting large-size injection molded products such as computer housings, office supplies, and the like.

A halogen-containing flame retardant and an antimony-containing compound can be added to the resin compositions to impart good flame retardancy. However, halogen-containing flame retardants can produce toxic gases during combustion. Therefore, there is an increased demand for the resin without a halogen flame retardant due to the harmful health effects of the gas.

A well known and widely used method of imparting flame retardancy without using halogen-containing flame retardants uses a phosphate ester flame retardant. U.S. Pat. No. 4,692,488 discloses a thermoplastic resin composition comprising a halogen-free aromatic polycarbonate resin, a halogen-free styrene-acrylonitrile copolymer, a halogen-free phosphorous compound, a tetrafluoroethylene polymer and a small amount of ABS copolymer. U.S. Pat. No. 5,061,745 also discloses a flame retardant resin composition comprising an aromatic polycarbonate resin, an ABS graft copolymer, a styrene copolymer, phosphate ester and a tetrafluoroethylene polymer. However, the resin compositions described above have a disadvantage in that it is necessary to add an excessive amount of phosphoric ester flame retardant in order to obtain an acceptable level of flame retardancy.

SUMMARY OF THE INVENTION

The present inventors have developed a flameproof polycarbonate resin composition which is environmentally friendly and does not cause generation of environmental pollutants. The composition of the invention includes a novel sterically hindered phenolic phosphonate added as a flame retardant to a thermoplastic resin. The present invention further provides an environmentally friendly flameproof polycarbonate resin composition exhibiting good flame retardancy, even when a small amount of flame retardant is used therein, by employing the sterically hindered phenolic phosphonate compound as a flame retardant An aspect of the present invention provides a sterically hindered phenolic phosphonate flame retardant having excellent flame retardancy. The novel phenolic phosphonate flame retardant can be used in a thermoplastic flameproof polycarbonate resin composition.

Other aspects, features and advantages of the present invention will be apparent from the ensuing disclosure and appended claims.

According to the present invention, there is provided a novel sterically hindered phenolic phosphonate compound. The phenolic phosphonate compound is represented by the following Chemical Formula 1.

[Chemical Formula 1]

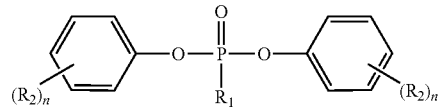

wherein $R_1$ is a $C_1$-$C_6$ alkyl or a $C_6$-$C_{14}$ aryl group; each $R_2$ is independently selected from a $C_1$-$C_6$ linear alkyl group or a $C_3$-$C_6$ branched alkyl group; and each n is independently 1 to 3.

Another aspect of the present invention relates to a method of preparing a sterically hindered phenolic phosphonate compound. The method comprises reacting a phenolic compound with a halogenated phosphonate compound.

In exemplary embodiments of the invention, the method may include reflux-reacting an equivalent of a halogenated phosphonate compound and two equivalents of a phenolic compound.

Another aspect of the invention provides a method of improving flame retardancy of a thermoplastic resin by adding the foregoing sterically hindered phenolic phosphonate compound as a flame retardant to the resin. In exemplary embodiments of the invention, the thermoplastic resin may comprise polycarbonate.

Another aspect of the invention provides a flameproof polycarbonate resin composition comprising a sterically hindered phenolic phosphonate compound. In some embodiments, the composition may include about 100 parts by weight of a base resin comprising a polycarbonate resin, and about 0.5 to about 20 parts by weight of a sterically hindered phenolic phosphonate compound.

In exemplary embodiments of the invention, the base resin may include about 50 to about 100% by weight of a polycarbonate resin and about 0 to about 50% by weight of a rubber modified styrenic resin.

In exemplary embodiments of the invention, the resin composition may further include an aromatic phosphate ester compound. The aromatic phosphate ester compound can be used in an amount of about 10 parts by weight or less based on 100 parts by weight of the base resin.

In exemplary embodiments of the invention, the resin composition may further include other additives such as plasticizers, heat stabilizers, anti-dripping agents, antioxidants, compatibilizers, light-stabilizers, pigments, dyes, inorganic fillers and combinations thereof.

Another aspect of the invention provides a molded article molded from the foregoing polycarbonate resin composition. The molded article may have an average combustion time of about 0.5 seconds or less after the first round of combustion measured for specimens having a thickness of about ⅛" and a size of about 125 mm by 13 mm in accordance with UL 94 VB.

DETAILED DESCRIPTION OF THE INVENTION

Figure 1C:
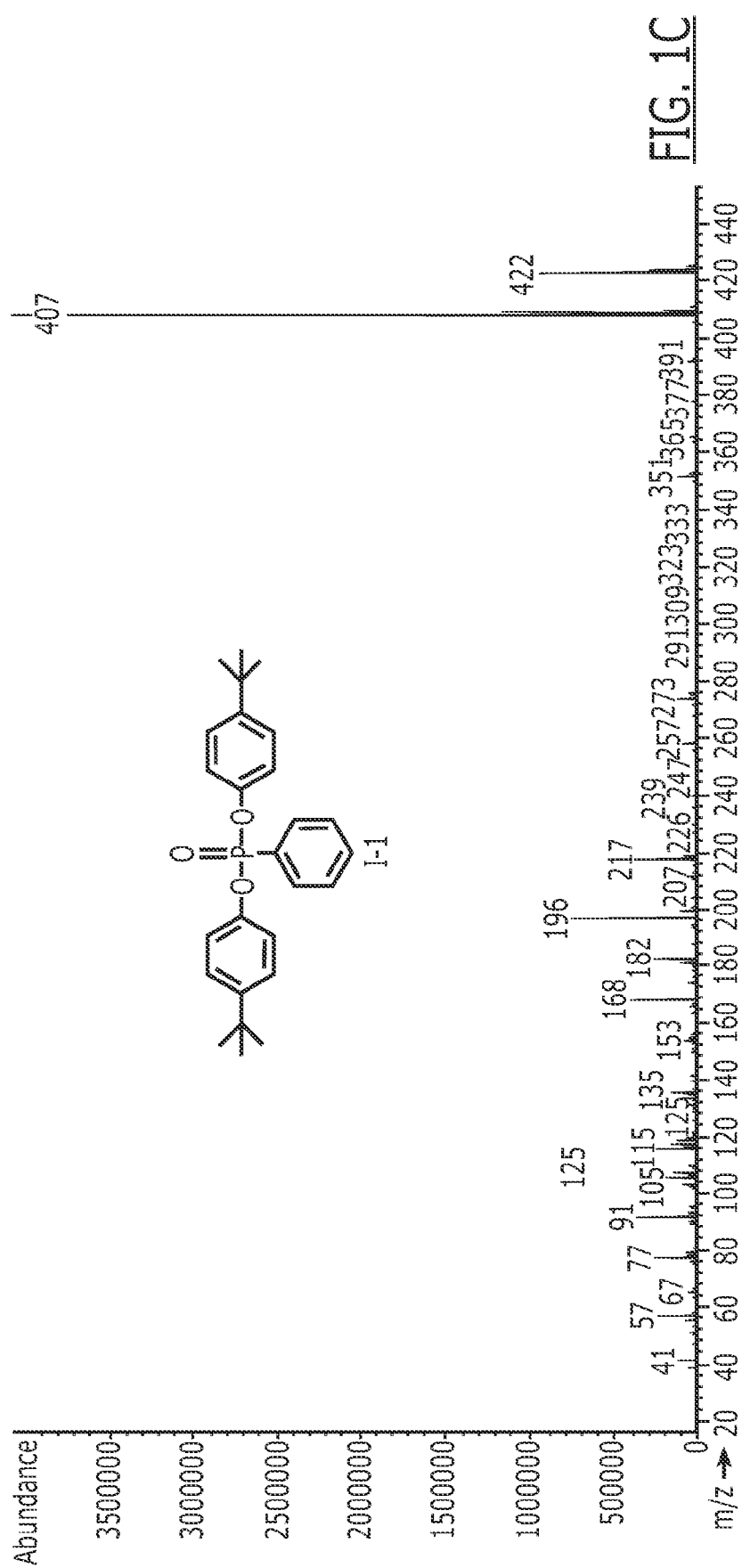
FIG. 1 shows a GC-MS chromatogram of a sterically hindered phenolic phosphonate compound c1 prepared in Example 1.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

Sterically Hindered Phenolic Phosphonate Compound

The sterically hindered phenolic phosphonate compound of the present invention may be represented by the following Chemical Formula 1.

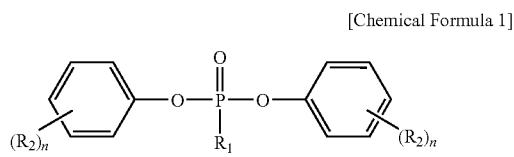

[Chemical Formula 1]

wherein $R_1$ is a $C_1$-$C_6$ alkyl group or a $C_6$-$C_{14}$ aryl group; each $R_2$ is independently a $C_1$-$C_6$ linear alkyl group or a $C_3$-$C_6$ branched alkyl group; and each n is independently 1-3.

In an exemplary embodiment, each $R_2$ is $C_1$-$C_6$ linear alkyl and n is 2 or 3 in Chemical Formula 1. In another exemplary embodiment, each $R_2$ is $C_3$-$C_6$ branched alkyl and n is 1 to 3. In other exemplary embodiments, $R_1$ is $C_6$-$C_{14}$ aryl.

Method of Preparing a Sterically Hindered Phenolic Phosphonate Compound

Another aspect of the present invention provides a method of preparing a sterically hindered phenolic phosphonate compound. The method includes reacting a phenolic compound and a halogenated phosphonate compound. In some embodiments, the sterically hindered phenolic phosphonate compound may be obtained by reflux-reacting a phenolic compound represented by the following Chemical Formula 2 and a halogenated phosphonate compound represented by the following Chemical Formula 3 for about 12 to about 48 hours in the presence of a base. In exemplary embodiments of the invention, the base may be used alone or in combination with a solvent. In an exemplary embodiment, the base may be, but is not limited to, pyridine, which can be used alone or in combination with toluene and triethylamine.

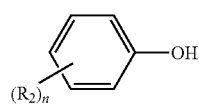

[Chemical Formula 2]

wherein each $R_2$ is independently a $C_1$-$C_6$ linear alkyl group or a $C_3$-$C_6$ branched alkyl group; and n is 1-3.

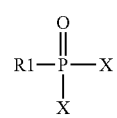

[Chemical Formula 3]

wherein $R_1$ is a $C_1$-$C_6$ alkyl group or a $C_6$-$C_{14}$ aryl group; and X is Cl or Br.

In exemplary embodiments of the invention, an equivalent of the halogenated phosphonate compound reacts with two equivalents of the phenolic compound. The compounds may be reflux-reacted at about 100 to about 200° C., for example about 120 to about 160° C., for about 12 to about 48 hours, for example about 18 to about 36 hours, in the presence of a base and a solvent.

Examples of the phenolic compound represented by Chemical Formula 2 may include, but are not limited to, 4-t-butyl phenol, 2,4,6-trimethyl phenol, 2,6-dimethyl phenol, and the like, and combinations thereof.

Examples of the halogenated phosphonate compound represented by Chemical Formula 3 may include, but are not limited to, phenyl dichlorophosphonate, phenyl dibromophosphonate and the like, and combinations thereof.

Thermoplastic Resin Composition Containing a Sterically Hindered Phenolic Phosphonate Compound Another aspect of the invention provides a method of improving flame retardancy of a thermoplastic resin by using the foregoing sterically hindered phenolic phosphonate compound as a flame retardant. When the sterically hindered phenolic phosphonate compound is added to the thermoplastic resin as a flame retardant, the thermoplastic resin can exhibit excellent flame retardancy even when a small amount of the flame retardant is used therein. In some embodiments, the method includes blending the sterically hindered phenolic phosphonate compound of the present invention with the thermoplastic resin. The thermoplastic resin may include a polycarbonate.

Another aspect of the invention provides a flameproof polycarbonate resin composition which contains the foregoing sterically hindered phenolic phosphonate compound. In exemplary embodiments of the invention, the resin composition comprises about 100 parts by weight of a base resin including a polycarbonate resin, and about 0.5 to about 20 parts by weight of the sterically hindered phenolic phosphonate compound. If the sterically hindered phenolic phosphonate compound is used in the range of less than about 0.5 parts by weight, sufficient flame retardancy may not be obtained, and if it is used in the range of more than about 20 parts by weight, the composition may exhibit low mechanical strength and low processability. In one embodiment, the sterically hindered phosphonate compound may be used in an amount of from about 1 part by weight to about 17 parts by weight, based on about 100 parts by weight of the base resin. In another embodiment, the sterically hindered phosphonate compound may be used in an amount of from about 4 to about 13 parts by weight, based on about 100 parts by weight of the base resin. In other embodiments, the sterically hindered phosphonate compound may be used in an amount of from about 10 to about 20 parts by weight, based on about 100 parts by weight of the base resin.

The polycarbonate resin used in the present invention may be an aromatic polycarbonate resin prepared by reacting a diphenol represented by the following Chemical Formula 4 with a phosgene, a halogen formate or a carboxylic acid diester.

[Chemical Formula 4]

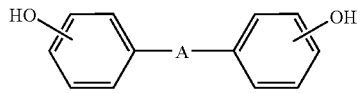

wherein A is a single bond, a $C_{1-5}$ alkylene group, a $C_{1-5}$ alkylidene group, a $C_{5-6}$ cycloalkylidene group, —S— or —$SO_2$—.

Examples of the diphenol may include without limitation hydroquinol, resorcinol, 4,4'-dihydroxy diphenyl, 2,2-bis-(4-hydroxyphenyl)-propane, 2,4-bis-(4-hydroxyphenyl)-2-methyl butane, 1,1-bis-(4-hydroxyphenyl)-cyclohexane, 2,2-bis-(3-chloro-4-hyroxyphenyl)-propane, 2,2-bis-(3,5-dichloro-4-hydroxyphenyl)-propane, and the like, and combinations thereof. Advantageous diphenols can include 2,2-bis-(4-hydroxyphenyl)-propane (also referred to as "bisphenol A"), 2,2-bis-(3,5-dichloro-4-hydroxyphenyl)-propane, and 1,1-bis-(4-hydroxyphenyl)-cyclohexane, and the like, and combinations thereof.

In the present invention, the polycarbonate resin (A) may have a weight average molecular weight (Mw) of about 10,000 to about 200,000, for example about 15,000 to about 80,000.

Suitable polycarbonates incorporated into the composition of the present invention may be branched in a known manner, for example, by incorporating about 0.05 to about 2 mol %, based to total quantity of diphenols used, of tri- or higher functional compounds, for example, those with three or more phenolic groups.

A homopolycarbonate, a copolycarbonate, or a combination thereof as a polycarbonate may be used in the present invention and a blend form of a copolycarbonate and a homopolycarbonate may also be used.

Some portion of the polycarbonate resin may be replaced with an aromatic polyester-carbonate resin that can be obtained by polymerization in the presence of an ester precursor, such as difunctional carboxylic acid.

In some embodiments, the base resin may include about 50 to about 100% by weight of a polycarbonate resin and about 0 to about 50% by weight of a rubber modified aromatic vinyl resin. When the rubber modified aromatic vinyl resin is used in the range of less than about 50% by weight, a good balance of properties such as flame retardancy and mechanical strength can be obtained. In exemplary embodiments, the rubber modified aromatic vinyl resin is used in the range of less than about 40% by weight.

The rubber modified aromatic vinyl resin according to some embodiments can be a polymer in which rubbery polymers are dispersed in the form of particles in a matrix (continuous phase) comprising an aromatic vinyl polymer.

The rubber modified aromatic vinyl resin may be prepared, for example, by polymerizing an aromatic vinyl monomer and a vinyl monomer copolymerizable with the aromatic vinyl monomer in the presence of a rubbery polymer. The rubber modified aromatic vinyl resin can be prepared by known methods such as emulsion polymerization, suspension polymerization, bulk polymerization, or extrusion of a graft copolymer resin with another copolymer resin. In some embodiments, the rubber modified aromatic vinyl resin can be produced by separately preparing a graft copolymer resin typically having high rubber content and an aromatic vinyl copolymer resin which does not contain rubber and mixing them together. In bulk polymerization, both a graft copolymer resin typically having high rubber content and an aromatic vinyl copolymer resin which does not contain rubber are prepared together in one process. Regardless of the polymerization technique used, the rubber content in a final rubber modified aromatic vinyl resin can be about 5 to about 30 parts by weight.

In exemplary embodiments of the invention, the rubber modified aromatic vinyl resin can be copolymer resins of acrylonitrile-butadiene-styrene (ABS), copolymer resins of acrylonitrile-acrylic rubber-styrene (AAS), copolymer resins of acrylonitrile-ethylene propylene rubber-styrene (AES), and the like, and combinations thereof.

In the rubber modified aromatic vinyl resin of the present invention, the graft copolymer resin can be used alone or in combination with the vinyl copolymer resin, depending on the compatibility thereof.

The graft copolymer resin may be prepared by graft-polymerizing about 5 to about 65% by weight of a rubbery polymer, about 30 to about 95% by weight of an aromatic vinyl monomer, about 1 to about 20% by weight of a monomer copolymerizable with the aromatic vinyl monomer, and about 0 to about 15% by weight of a monomer for providing processability and heat resistance.

Examples of the rubbery polymers may include without limitation diene-rubbers such as polybutadiene, poly(styrene-butadiene), poly(acrylonitrile-butadiene) and the like; saturated rubbers in which hydrogen is added to the diene-rubbers; isoprene rubbers, chloroprene rubbers; acrylic rubbers such as polybutyl acrylic acid; terpolymers of ethylene-propylene-diene (EPDM), and the like, and combinations thereof. The rubbers may be used alone or in combination with one another. The average size of the rubber particles can range from about 0.1 to about 4 μm taking into account the desired impact strength and appearance of the resin composition.

Examples of the aromatic vinyl monomer may include without limitation styrene, α-methyl styrene, β-methyl styrene, p-methyl styrene, p-t-butyl styrene, ethyl styrene, vinyl xylene, monochlorostyrene, dichlorostyrene, dibromostyrene, vinyl naphthalene, and the like, and combinations thereof. These aromatic vinyl monomers can be used alone or in combination with one another.

Examples of the monomer copolymerizable with the aromatic vinyl monomer may include without limitation cyanide vinyl-containing monomer such as acrylonitrile and unsaturated nitrile-containing compounds such as ethacrylonitrile, methacrylonitrile, and the like, and combinations thereof. These monomers may be used alone or in combination with one another.

The graft copolymer resin may also include other monomers such as but not limited to acrylic acid, methacrylic acid, maleic acid anhydride, N-substituted maleimide, and the like, and combinations thereof, in order to impart good processability and heat resistance.

The vinyl copolymer resin may be prepared by copolymerizing about 60 to about 90% by weight of an aromatic vinyl monomer, about 10 to about 40% by weight of a monomer copolymerizable with the aromatic vinyl monomer and about 0 to about 30% by weight of a monomer providing process ability and heat resistance.

Examples of the aromatic vinyl monomer may include without limitation styrene, α-methyl styrene, β-methyl styrene, p-methyl styrene, p-t-butyl styrene, ethylstyrene, vinyl xylene, monochlorostyrene, dichlorostyrene, dibromostyrene, vinyl naphthalene, and the like, and combinations thereof. These aromatic vinyl monomers can be used alone or in combination with one another.

Examples of the monomer copolymerizable with the aromatic vinyl monomer may include without limitation cyanide vinyl-containing monomer such as acrylonitrile and unsaturated nitrile-containing compounds such as ethacrylonitrile and methacrylonitrile, and the like, and combinations thereof. These may be used alone or in combination with one another.

The vinyl copolymer resin may also include other monomers such as but not limited to acrylic acid, methacrylic acid, maleic acid anhydride, N-substituted maleimide, and the like, and combinations thereof, in order to impart processability and heat resistance.

In some embodiments, the rubber modified aromatic vinyl resin may comprise about 20 to about 100% by weight of a graft copolymer resin and about 0 to about 80% by weight of a vinyl copolymer resin, for example about 20 to about 50% by weight of a graft copolymer resin and about 50 to about 80% by weight of a vinyl copolymer resin.

In some embodiments, the resin composition may further include an aromatic phosphate ester compound. The aromatic phosphate ester compound may be represented by the following Chemical Formula 5.

[Chemical Formula 5]

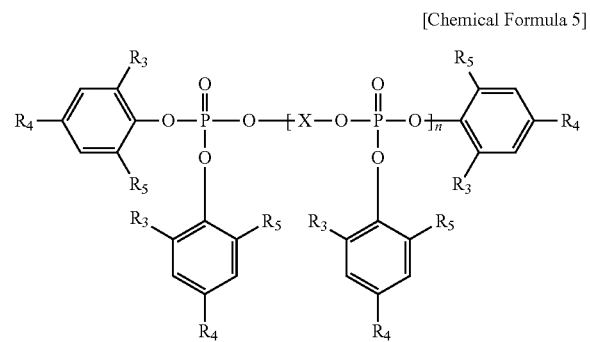

wherein $R_3$, $R_4$, and $R_5$ are each independently hydrogen or a $C_1$-$C_4$ alkyl group; X is a $C_6$-$C_{20}$ aryl group or a $C_1$-$C_{10}$ alkyl-substituted $C_6$-$C_{20}$ aryl group derived from resorcinol, hydroquinol, and bisphenol-A; and n is 0 to 4.)

When n is 0, the compounds represented in Chemical Formula 5 can include without limitation triphenyl phosphate, tri(2,6-dimethyl) phosphate, and the like, and where n is 1, the compounds can include without limitation resorcinol bis(diphenyl) phosphate, resorcinol bis(2,6-dimethyl phenyl) phosphate, resorcinol bis(2,4-ditertiary butyl phenyl) phosphate, hydroquinol bis(2,6-dimethyl phenyl) phosphate, hydroquinol bis(2,4-ditertiary butyl phenyl) phosphate, and the like. The aromatic phosphate ester compounds can be used alone or in combination therewith.

The aromatic phosphate ester compound according to the present invention can be used in an amount of about 10 parts by weight or less, for example about 7 parts by weight or less, and as another example about 5 parts by weight or less, based on about 100 parts by weight of the base resin.

The resin composition according to the present invention may further include other additives depending on its use. Examples of such additives may include without limitation plasticizers, heat stabilizers, antioxidants, anti-dripping agents, compatibilizers, light-stabilizers, pigments, dyes, inorganic fillers and the like. The additives can be used alone or in combination with one another. Examples of the inorganic fillers added include asbestos, glass fibers, talc, ceramic and sulfates. The additives can be added in an amount of about 30 parts by weight or less based on the total resin composition.

The resin composition of the present invention can be prepared by conventional methods.

Another aspect of the invention provides a molded article molded from the foregoing polycarbonate resin composition. Molding methods may include, without limitation, extrusion, injection, vacuum molding, blow molding, casting molding and the like, but are not limited to these methods. Since the molded article has excellent impact resistance and flame retardancy, it is well suitable for exterior parts of electronic goods and precise parts of automobiles.

In some embodiments, the molded article can have an average combustion time of about 0.5 seconds or less which is measured after a first round of combustion measured for test specimens having a size of about 125 mm×13 mm and a thickness of about ⅛" inch in accordance with UL 94 VB. The polycarbonate resin composition according to the present invention is suitable for housings of electric/electronic goods such as televisions, washing machines, dishwashers, computers, audio sets, video players, CD players, cellular phones, telephones, and the like or vehicle parts such as dashboard panels, door linings, bumpers, battery covers, distributor caps, heater panels and the like, since it has good impact resistance, flowability, flexural strength, chemical resistance and light resistance.

The invention may be better understood by reference to the following examples which are intended for the purpose of illustration and are not to be construed as in any way limiting the scope of the present invention, which is defined in the claims appended hereto.

EXAMPLES

Example 1-3

Preparation of a Sterically Hindered Phenolic Phosphonate (c1) Example 1

Figure 2:
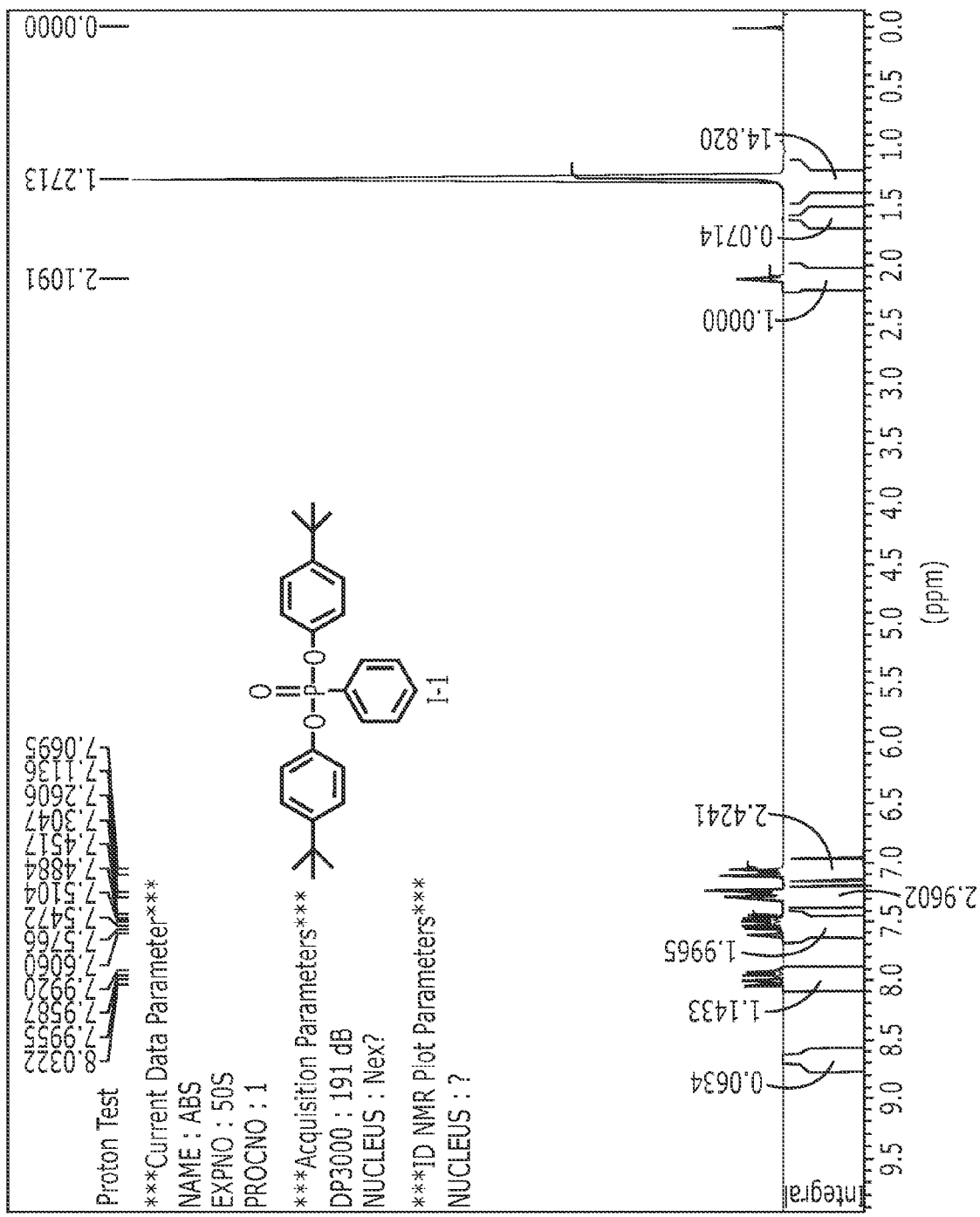
FIG. 2 shows a $^1$H-NMR spectrum of the sterically hindered phenolic phosphonate compound c1 prepared in Example 1.

4-t-butyl phenol (60 g, 0.40 mol), phenyl phosphonic dichloride (43 g, 0.20 mol), and pyridine (400 mL) are charged into a vessel, and refluxed under stirring at 140° C. for about 24 hours. The temperature of the vessel is cooled to room temperature and then pyridine is distilled under reduced pressure using a rotary distillation apparatus. When only solid remains in the vessel, 500 mL of distilled water is then added to the vessel and stirred for 1 hour. During the process, pyridine.chloric acid salt produced from the reaction is dissolved in the water and an insoluble solid compound (c1) is filtered. The filtered solid is dried for 24 hours in an oven under reduced pressure to obtain a white solid (c1) 79 g with 94% purity. The resultant compound (c1) is analyzed by GC-MS and $^1$H-NMR, and the results are shown in FIGS. 1 and 2, respectively.

(c2) Example 2

Figures 3B, 3C:
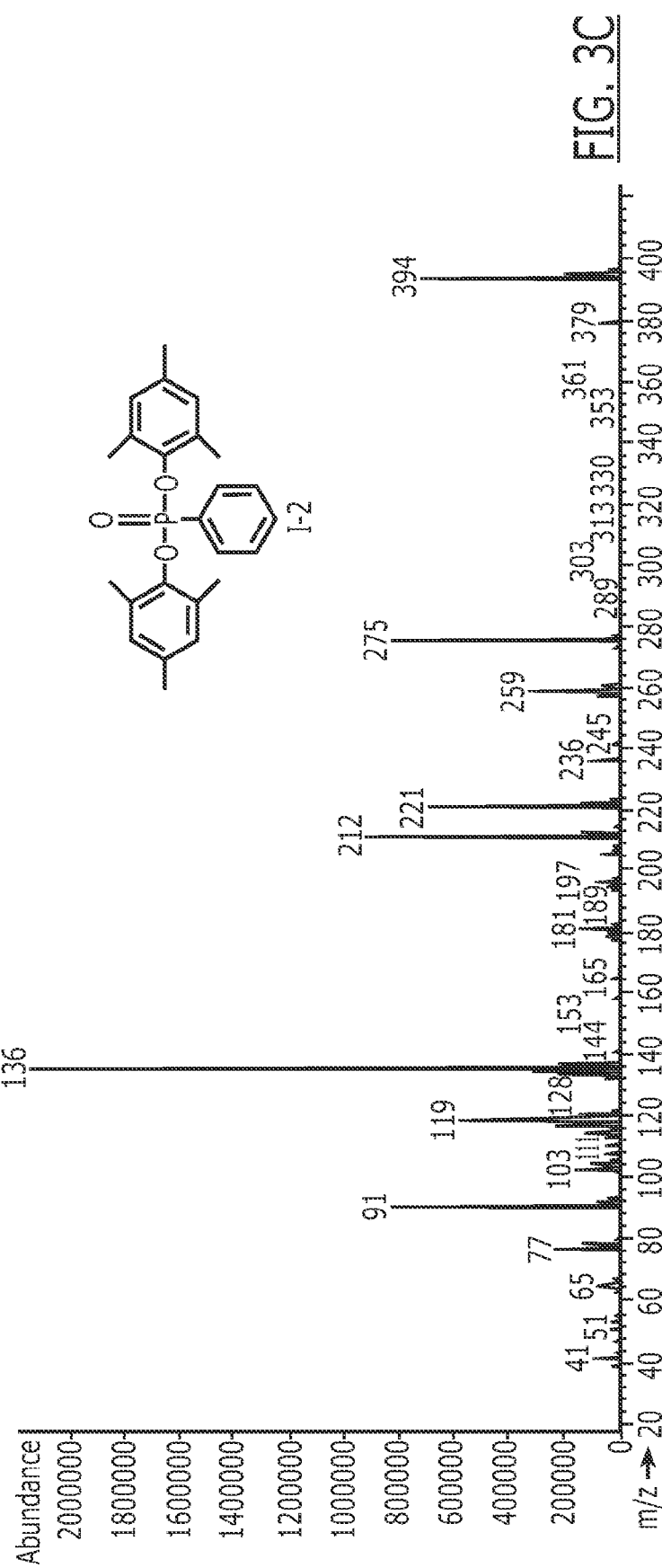
FIG. 3 shows a GC-MS chromatogram of a sterically hindered phenolic phosphonate compound c2 prepared in Example 2.
Figure 4:
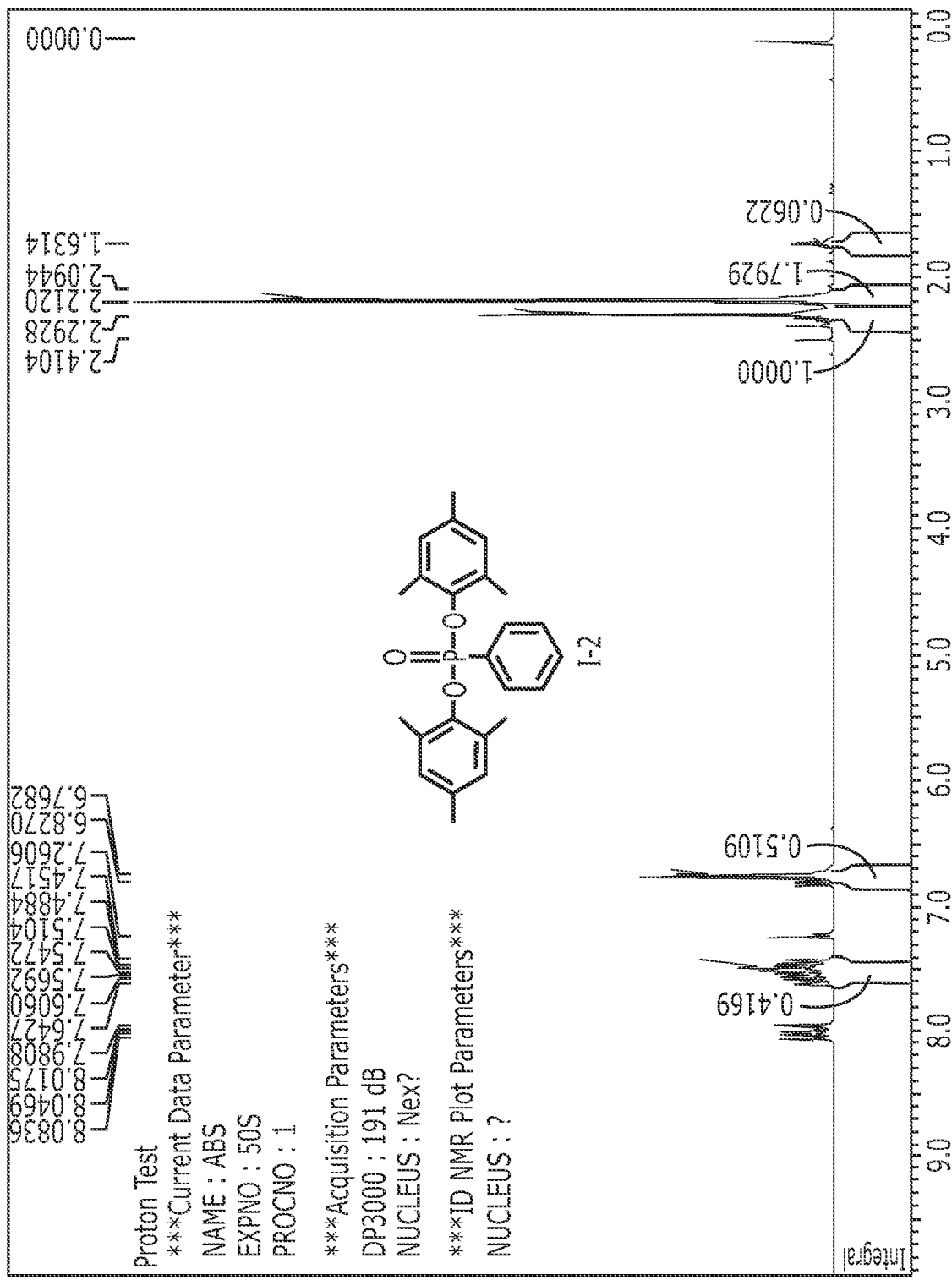
FIG. 4 shows a $^1$H-NMR spectrum of the sterically hindered phenolic phosphonate compound c2 prepared in Example 2.

2, 4, 6-trimethyl phenol (54 g, 0.40 mol), phenyl phosphonic dichloride (43 g, 0.20 mol), and pyridine (400 mL) are charged into a vessel, and refluxed under stirring at 140° C. for about 24 hours. The temperature of the vessel is cooled to room temperature and then pyridine is distilled under reduced pressure using a rotary distillation apparatus. When only solid remained in the vessel, 500 mL of distilled water is then added to the vessel and stirred for 1 hour. During the process, pyridine.chloric acid salt produced in the reaction is dissolved in the water and an insoluble solid compound (c2) is filtered. The filtered solid is dried for 24 hours in the oven under reduced pressure to obtain a white solid (c2) 75.7 g with 96% purity. The resultant compound (c2) is analyzed by GC-MS and $^1$H-NMR, and the results are shown in FIGS. 3 and 4, respectively.

(c3) Example 3

Figure 5A:
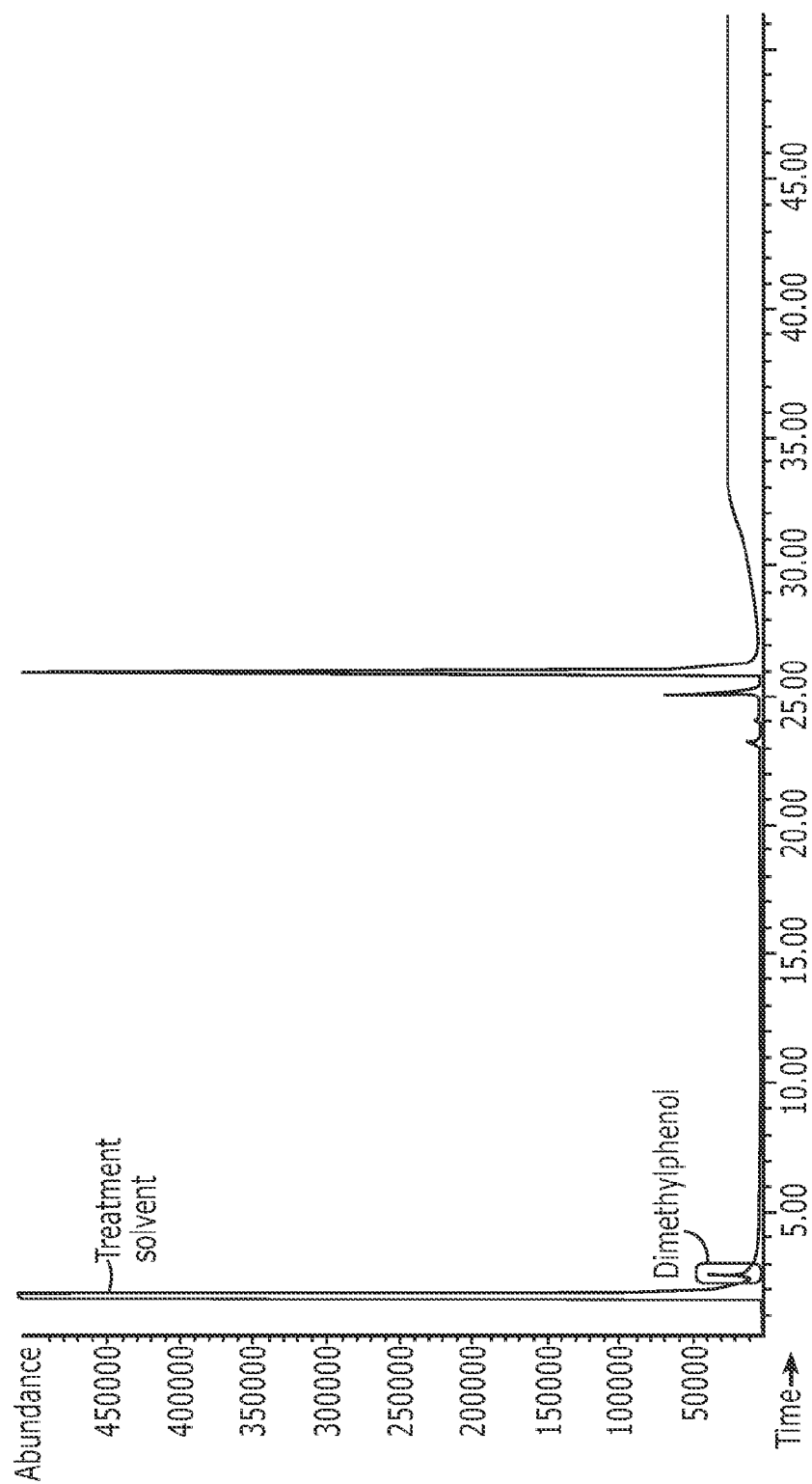
FIG. 5 shows a GC-MS chromatogram of a sterically hindered phenolic phosphonate compound c3 prepared in Example 3.
Figures 5B, 5C:
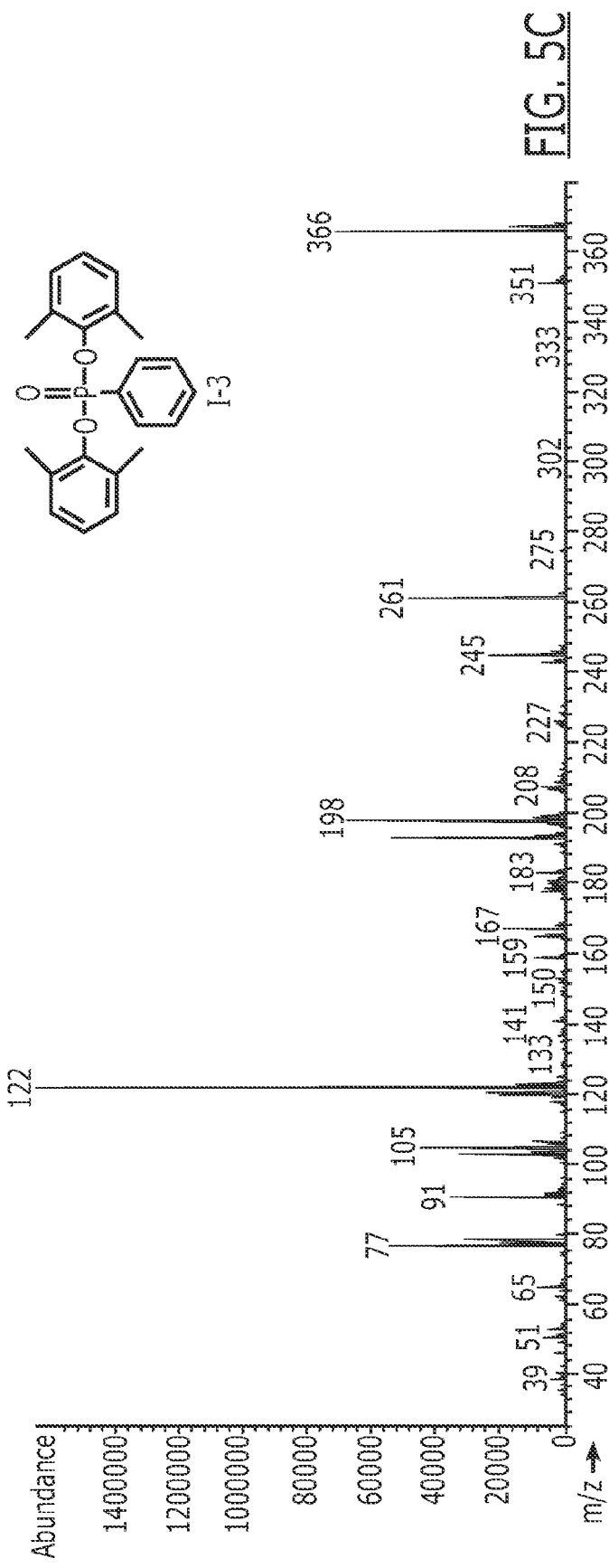
Figure 6:
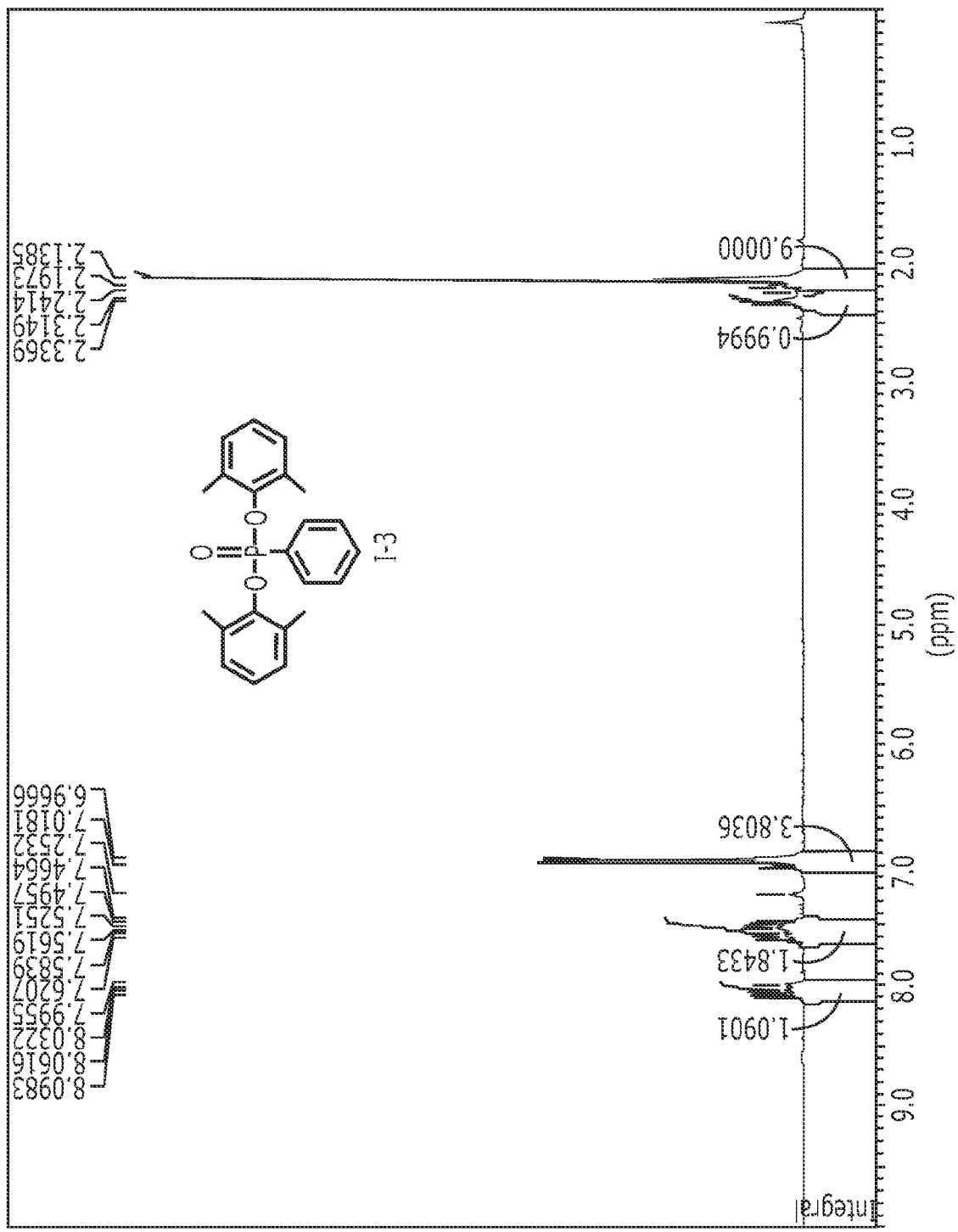
FIG. 6 shows a $^1$H-NMR spectrum of the sterically hindered phenolic phosphonate compound c3 prepared in Example 3.

2,6-dimethyl phenol (50 g, 0.40 mol), phenyl phosphonic dichloride (43 g, 0.20 mol), and pyridine (400 mL) are charged into a vessel, and refluxed under stirring at 140° C. for about 24 hours. The temperature of the vessel is cooled to room temperature and then pyridine is distilled under reduced pressure using a rotary distillation apparatus. When only solid remained in the vessel, 500 mL of distilled water is then added to the vessel and stirred for 1 hour. During the process, pyridine.chloric acid salt produced in the reaction is dissolved in the water and an insoluble solid compound (c3) is filtered. The filtered solid is dried for 24 hours in the oven under reduced pressure to obtain a white solid (c3) 69 g with 95% purity. The resultant compound (c3) is analyzed by GC-MS and $^1$H-NMR, and the results of analysis are shown in FIGS. 5 and 6, respectively.

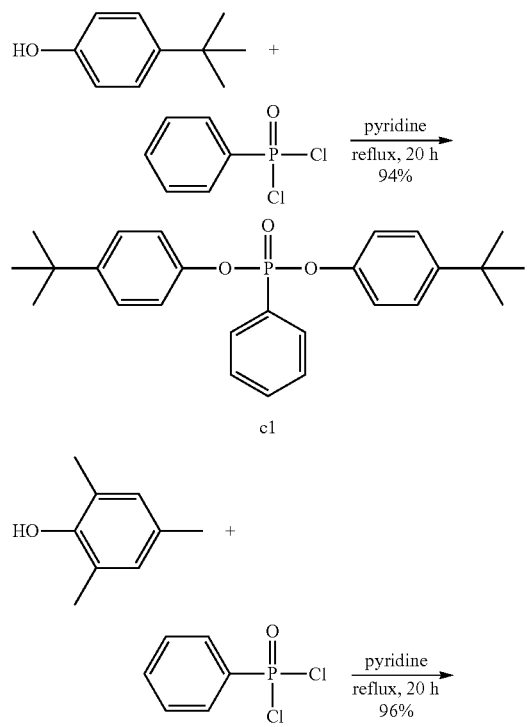

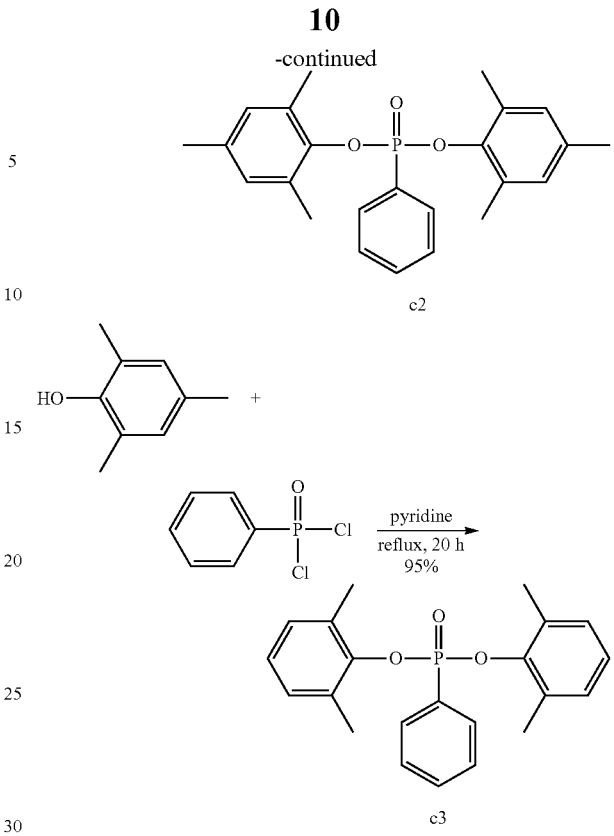

Examples 4-9

Preparation of Thermoplastic Resin Composition Using a Sterically Hindered Phenolic Phosphonate Each component used in the following examples and comparative examples are as follows.

(A) Polycarbonate Resin

Bisphenol-A based polycarbonate with a weight average molecular weight of 25,000 (Mw) made by Teijin Chemicals Ltd. of Japan (product name: Panlite L'1250 AP) is used.

(B) Rubber Modified Styrenic Resin (B1) Graft Copolymer Resin 50 parts by weight of butadiene rubber latex, 36 parts by weight of styrene which is a graft-polymerizable monomer, 14 parts by weight of acrylonitrile, and 150 parts by weight of deionized water are mixed. To the mixture, 1.0 part by weight of potassium oleate, 0.4 parts by weight of cumen hydroperoxide, 0.2 parts by weight of mercaptan-containing chain transfer agent, 0.4 parts by weight of glucose, 0.01 parts by weight of ferrous sulfate hydrate, and 0.3 parts by weight of sodium pyrophosphate are added. The blend is kept at 75° C. for 5 hours to obtain g-ABS latex. To the g-ABS latex, 0.4 parts by weight of sulfuric acid is added and coagulated and then dried to obtain a rubber modified polystyrene resin (g-ABS) in a powder form.

(B2) Vinyl Copolymer Resin 75 parts by weight of styrene, 25 parts by weight of acrylonitrile, and 120 parts by weight of deionized water are mixed. To the mixture, 0.2 parts by weight of azobisisobutylonitrile (AIBN), 0.4 parts by weight of tricalcium phosphate and 0.2 parts by weight of mercaptan-containing chain transfer agent are added. The resultant solution is heated to 80° C. for 90 minutes and kept for 180 minutes. The resultant product is washed, dehydrated and dried. Styrene-acrylonitrile copolymer (SAN) in a powder form is then obtained. The styrene-acrylonitrile copolymer (SAN) has a weight average molecular weight (Mw) of about 80,000 to about 100,000.

(C) Sterically Hindered Phenolic Phosphonate

Sterically hindered phenolic phosphonates (C1), (C2) and (C3) prepared in the above Examples 1-3 are used.

(D) Aromatic Phosphate Ester Compound

Tetra-2,6-dimethyl phenyl resorcinol diphosphate made by Daihachi Chemical Industry Co., Ltd. of Japan (product name: PX-200) is used.

Examples 4-9

The components as shown in Table 1 are added to a conventional mixer, and the mixture is extruded through a conventional twin screw extruder at a temperature range of 200-280° C. to prepare a product in pellet form. The pellets are dried at 80° C. for 2 hours and then molded into test specimens for flame retardancy in an injection molding machine at 180-280° C. with a mold temperature of 40-80° C. Flame retardancy is determined by measuring the average combustion time for the specimens having a thickness of about ⅛" and a size of 125 mm by 13 mm in accordance with UL 94 VB.

Comparative Examples 1-2

Comparative Examples 1-2 are conducted in the same manner as in the Examples above except each component is used in a different amount. The results of comparative Examples 1-2 are shown in Table 1.

TABLE 1

|  |  | Examples | | | | |
|---|---|---|---|---|---|---|
|  |  | 4 | 5 | 6 | 7 | 8 |
| (A) PC resin |  | 100 | 100 | 100 | 100 | 100 |
| (B) ABS resin | (B1) | — | — | — | — | — |
|  | (B2) | — | — | — | — | — |
| (C) Phenolic | C1 | 3 | 5 | — | — | — |
| phosphonate | C2 | — | — | 3 | 5 | — |
|  | C3 | — | — | — | — | 5 |
| (D) Aromatic phosphate ester |  | — | — | — | — | — |
| First average combustion time (⅛"), seconds |  | 0.0 | 0.0 | 0.0 | 0.0 | 0.5 |
| Second average combustion time (⅛"), seconds |  | 9.3 | 5.3 | 3.3 | 0.0 | 8.8 |

As shown in Table 1, it can be seen that Examples employing a sterically hindered phenolic phosphonate exhibit good flame retardancy, compared to Comparative Examples using only aromatic phosphate ester compounds.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A sterically hindered phenolic phosphonate compound represented by the following Chemical Formula 1:

[Chemical Formula 1]

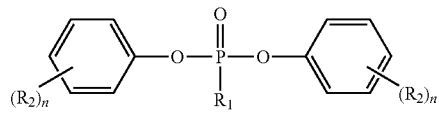

wherein $R_1$ is a $C_1$-$C_6$ alkyl group or a $C_6$-$C_{14}$ aryl group; each $R_2$ is independently a $C_1$-$C_6$ linear alkyl group or a $C_3$-$C_6$ branched alkyl group; and each n is 3.

2. A sterically hindered phenolic phosphonate compound of claim 1, wherein at least one $R_2$ is a $C_3$-$C_6$ branched alkyl and $R_1$ is $C_6$-$C_{14}$ aryl.

3. A sterically hindered phenolic phosphonate compound of claim 2, wherein at least one $R_2$ is t-butyl.

4. A sterically hindered phenolic phosphonate compound of claim 3, wherein each $R_2$ is t-butyl.

5. A sterically hindered phenolic phosphonate compound of claim 1, wherein at least one $R_2$ is $C_1$-$C_6$ linear alkyl and $R_1$ is $C_6$-$C_{14}$ aryl.

6. A sterically hindered phenolic phosphonate compound of claim 5, wherein at least one $R_2$ is methyl.

7. A sterically hindered phenolic phosphonate compound of claim 6, wherein each $R_2$ is methyl.

8. A method of preparing a sterically hindered phenolic phosphonate compound comprising reacting a phenolic compound represented by the following Chemical Formula 2 with a halogenated phosphonate compound represented by the following Chemical Formula 3

[Chemical Formula 2]

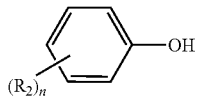

wherein each $R_2$ is independently a $C_1$-$C_6$ linear alkyl group or a $C_3$-$C_6$ branched alkyl group; and n is 3,

[Chemical Formula 3]

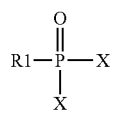

wherein $R_1$ is a $C_1$-$C_6$ alkyl group or a $C_6$-$C_{14}$ aryl group; and X is Cl or Br.

9. The method of claim 8, wherein said sterically hindered phenolic phosphonate compound is prepared by reflux-reacting an equivalent of a halogenated phosphonate compound and two equivalents of a phenolic compound.

10. A method of improving flame retardancy of a thermoplastic resin comprising adding a sterically hindered phenolic phosphonate compound as defined in claim 1 as a flame retardant to said thermoplastic resin.

11. The method of claim 10, wherein said thermoplastic resin comprises a polycarbonate.

12. A flameproof polycarbonate resin composition comprising:
  about 100 parts by weight of a base resin comprising a polycarbonate resin; and
  about 0.5 to about 20 parts by weight of a sterically hindered phenolic phosphonate compound represented by the following Chemical Formula 1:

[Chemical Formula 1]

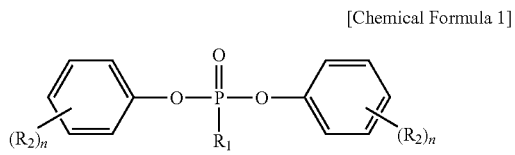

wherein $R_1$ is $C_1$-$C_6$ alkyl or $C_6$-$C_{14}$ aryl; each $R_2$ is independently $C_1$-$C_6$ linear alkyl or $C_3$-$C_6$ branched alkyl; and each n is 3.

13. The flameproof polycarbonate resin composition of claim 12, wherein said base resin comprises about 50 to about 100% by weight of a polycarbonate resin and about 0 to about 50% by weight of a rubber modified styrenic resin.

14. The flameproof polycarbonate resin composition of claim 13, wherein said rubber modified styrenic resin comprises about 20 to about 100% by weight of a graft copolymer resin and about 0 to about 80% by weight of a vinyl copolymer resin.

15. The flameproof polycarbonate resin composition of claim 14, wherein:

said graft copolymer resin is prepared by graft-polymerizing about 5 to about 65% by weight of a rubbery polymer, about 30 to about 95% by weight of an aromatic vinyl monomer, about 1 to about 20% by weight of a monomer copolymerizable with the aromatic vinyl monomer, and about 0 to about 15% by weight of a monomer for providing processability and heat resistance; and said vinyl copolymer resin is prepared by copolymerizing about 60 to about 90% by weight of an aromatic vinyl monomer, about 10 to about 40% by weight of a monomer copolymerizable with the aromatic vinyl monomer and about 0 to about 30% by weight of a monomer for providing processability and heat resistance.

16. The flameproof polycarbonate resin composition of claim 12, further comprising about 10 parts by weight or less of an aromatic phosphate ester compound represented by the following Chemical Formula 5 based on 100 parts by weight of the base resin

[Chemical Formula 5]

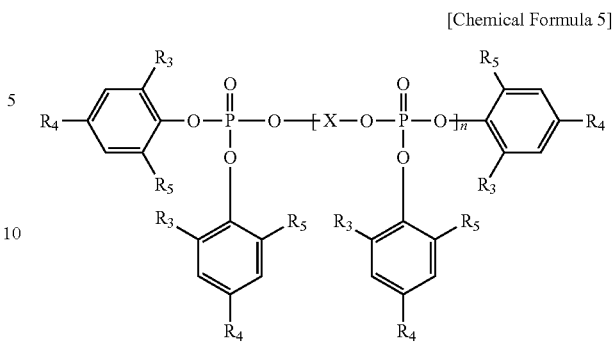

wherein each $R_3$, $R_4$, and $R_5$ is independently hydrogen or a $C_1$-$C_4$ alkyl group; X is a $C_6$-$C_{20}$ aryl group or a $C_1$-$C_{10}$ alkyl-substituted $C_6$-$C_{20}$ aryl group; and n is 0-4.

17. The flameproof polycarbonate resin composition of claim 12, further comprising at least one additive selected from the group consisting of plasticizers, heat stabilizers, antioxidants, anti-dripping agents, compatibilizers, light-stabilizers, pigments, dyes, inorganic fillers and combinations thereof 18. A molded article molded from the polycarbonate resin composition as defined in claim 12, wherein the molded article has an average combustion time of about 0.5 seconds or less after a first round of combustion measured for specimens having a thickness of about 1/8" and a size of about 125 mm by 13 mm in accordance with UL 94 VB.

19. The flameproof polycarbonate resin composition of claim 12, wherein at least one $R_2$ is a $C_3$-$C_6$ branched alkyl and $R_1$ is $C_6$-$C_{14}$ aryl.

20. The flameproof polycarbonate resin composition of claim 19, wherein at least one $R_2$ is t-butyl.

21. The flameproof polycarbonate resin composition of claim 20, wherein each $R_2$ is t-butyl.

22. The flameproof polycarbonate resin composition of claim 12, wherein at least one $R_2$ is $C_1$-$C_6$ linear alkyl and $R_1$ is $C_6$-$C_{14}$ aryl.

23. The flameproof polycarbonate resin composition of claim 22, wherein at least one $R_2$ is methyl.

24. The flameproof polycarbonate resin composition of claim 23, wherein each $R_2$ is methyl.

* * * * *